(12) United States Patent
Tolman et al.

(10) Patent No.: US 9,718,763 B2
(45) Date of Patent: Aug. 1, 2017

(54) CATALYTIC ESTER DECARBONYLATION

(71) Applicant: Regents of the University of Minnesota, Minneapolis, MN (US)

(72) Inventors: William Baker Tolman, Minneapolis, MN (US); Marc A. Hillmyer, Minneapolis, MN (US); Alex John, Minneapolis, MN (US); Levi Thomas Hogan, Olathe, KS (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/990,308

(22) Filed: Jan. 7, 2016

(65) Prior Publication Data

US 2016/0194276 A1    Jul. 7, 2016

Related U.S. Application Data

(60) Provisional application No. 62/100,713, filed on Jan. 7, 2015.

(51) Int. Cl.
*C07C 253/30* (2006.01)
*C07C 67/32* (2006.01)
(Continued)

(52) U.S. Cl.
CPC ............ *C07C 253/30* (2013.01); *B01J 27/13* (2013.01); *C07C 1/207* (2013.01); *C07C 17/361* (2013.01);
(Continued)

(58) Field of Classification Search
CPC .................................................. C07C 253/30
See application file for complete search history.

(56) References Cited

U.S. PATENT DOCUMENTS

2006/0211603 A1* 9/2006 Raju .................. C07K 9/008
514/2.9

\* cited by examiner

*Primary Examiner* — Shawquia Jackson
(74) *Attorney, Agent, or Firm* — Schwegman, Lundberg & Woessner, P.A.

(57) ABSTRACT

A process of preparing olefins of the formula (I) is described herein:

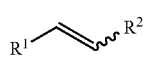

(I)

with $R^1$ being a substituted or unsubstituted ($C_1$-$C_{30}$)hydrocarbyl, and $R^2$ being a substituted or unsubstituted ($C_1$-$C_{20}$) hydrocarbyl. The process includes reacting a compound of formula (II)

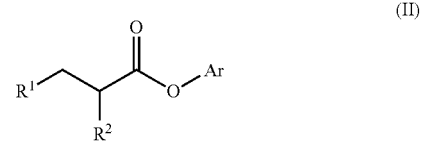

(II)

wherein Ar is chosen from

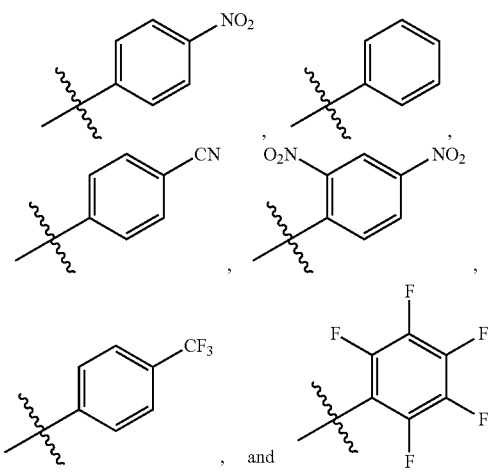

in the presence of a palladium-based catalyst and an organic solvent.

A process of preparing olefins of the formula (III) is also described:

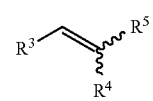

(III)

with $R^3$ being a substituted or unsubstituted ($C_1$-$C_{30}$)hydrocarbyl, $R^4$ being a substituted or unsubstituted ($C_1$-$C_{20}$) hydrocarbyl, and $R^5$ being a substituted or unsubstituted ($C_1$-$C_{30}$) hydrocarbyl. The process includes reacting a compound of formula (IV)

(IV)

(Continued)

wherein Ar is chosen from
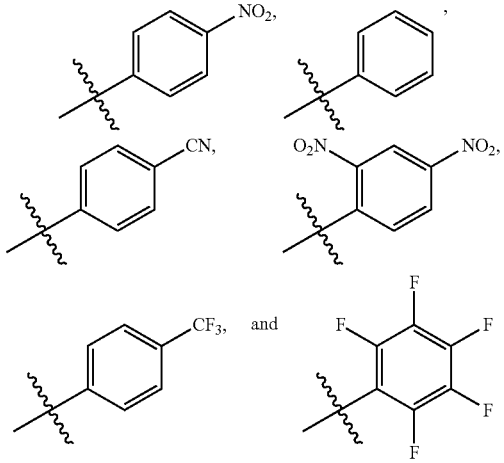
with a compound of formula (V)
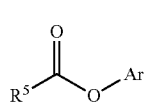
(V)
wherein Ar is chosen from
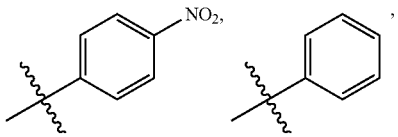
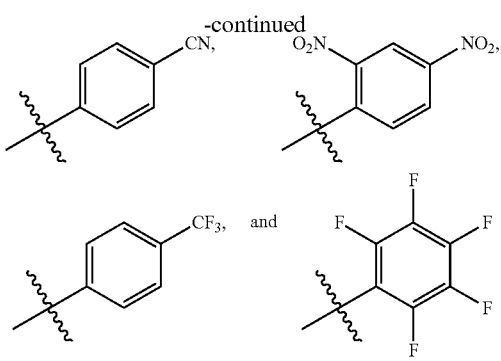
in the presence of a palladium-based catalyst and an organic solvent.
21 Claims, 1 Drawing Sheet
(51) Int. Cl.
  *B01J 27/13* (2006.01)
  *C07C 67/317* (2006.01)
  *C07C 201/12* (2006.01)
  *C07C 1/207* (2006.01)
  *C07C 17/361* (2006.01)
(52) U.S. Cl.
  CPC ............ *C07C 67/317* (2013.01); *C07C 67/32* (2013.01); *C07C 201/12* (2013.01); *B01J 2531/824* (2013.01); *C07C 2527/13* (2013.01); *C07C 2531/24* (2013.01); *Y02P 20/52* (2015.11)

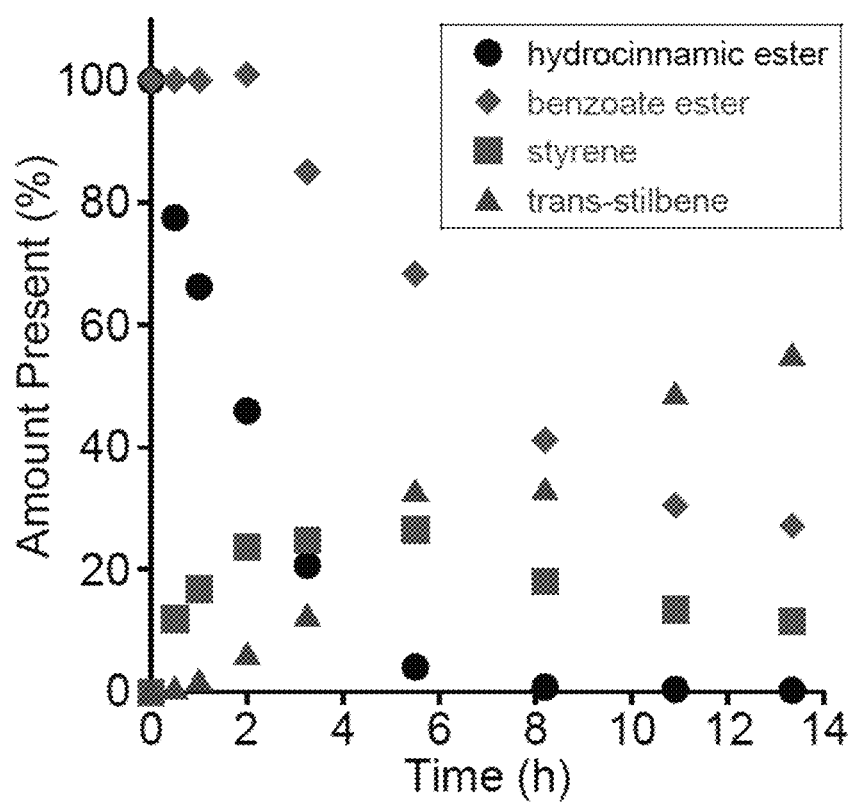

CATALYTIC ESTER DECARBONYLATION

CROSS-REFERENCE TO RELATED APPLICATION

This application claims the benefit of priority under 35 U.S.C. §119(e) of U.S. Provisional Patent Application 62/100,713 filed on Jan. 7, 2015, which application is incorporated by reference herein in its entirety.

STATEMENT OF GOVERNMENT SUPPORT

This invention was made with government support under CHE-1413862 awarded by the National Science Foundation. The government has certain rights in the invention.

BACKGROUND

Biomass, and chemicals derived therefrom, hold promise in transitioning to a more sustainable bio-based economy. Carboxylic acids can be used as starting materials for the synthesis of a variety of potentially useful compounds. For example, polymerizable olefins can be accessed through transition metal catalyzed dehydrative decarbonylation of aliphatic carboxylic acids. Such reactions often employ Pd, Rh, or Ir catalysts and phosphine-based ligands, with some recent attention to use of base metals like Fe and Ni. These processes typically use a sacrificial stoichiometric anhydride, like acetic ($Ac_2O$) or pivalic anhydride ($Piv_2O$), which activates the carboxylic acid substrate by forming a mixed anhydride that can readily undergo oxidative addition to the metal center.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 illustrates the progress of an example decarbonylation Heck-type coupling between hydrocinnamic ester and benzoate ester.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000.1" is equivalent to "0.0001."

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety, and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups: a nitrogen atom in groups such as amines, hydroxyamines, nitriles, nitro groups. N-oxides, hydrazides, azides, and enamines; and other heteroatoms in various other groups.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neo-pentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The terms "alkenyl" and "olefin." as used herein refers to straight and branched chain and cyclic alkyl groups as defined herein, except that at least one double bond exists between two carbon atoms. The terms "alkenyl" and "olefin" may be used interchangeably herein. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)—CH(CH$_3$), —C(CH$_2$CH$_3$)═CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl biphenyl, indacenyl, fluorenyl, phenanthrenyl, triphenylenyl, pyrenyl, naphthacenyl chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, $—NHR$, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "solvent" as used herein refers to a liquid that can dissolve a solid, another liquid, or a gas. Non-limiting examples of solvents are silicones, organic compounds, water, alcohols, ionic liquids, and supercritical fluids.

The term "room temperature" as used herein refers to a temperature of about 15° C. to about 28° C.

The term "standard temperature and pressure" as used herein refers to 20° C., and 101 kPa.

Process of Catalytic Ester Decarbonylation

In various embodiments, a process of preparing olefins of the formula (I) is described herein.

(I)

The variable $R^1$ is chosen from a substituted or unsubstituted $(C_1-C_{30})$hydrocarbyl. The variable $R^2$ is chosen from a substituted or unsubstituted $(C_1-C_{20})$hydrocarbyl. The process includes reacting a compound of formula (II)

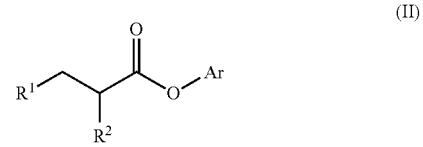

(II)

in which $R^1$ and $R^2$ are as described above. The variable Ar is chosen from

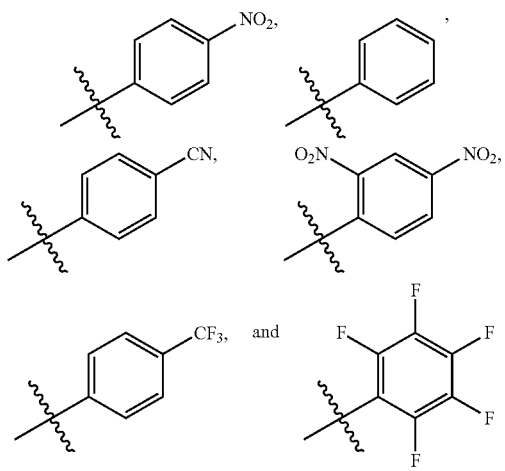

The reacting of compound (II) occurs in the presence of a catalyst, such as a palladium-based catalyst, and an organic solvent. In various embodiments, the preparation of the olefin of formula (I) occurs in the absence of any added ligands, such as phosphine ligands. The absence of added ligands, such as phosphine ligands, can make the process more economical and with less negative environmental impact.

In various embodiments, the palladium-based catalyst can be formed in situ from a palladium(0) precursor (e.g., $Pd_2(dba)_3$). In some embodiments, the palladium based catalyst can be a palladium halide (e.g., $PdCl_2$). In some embodiments, the palladium-based catalyst can be chosen from $PdCl_2$, $Pd_2(dba)_3$, $PdI_2$, $PdBr_2$ and $(COD)PdCl_2$ In various embodiments, the reacting of the compound of formula (II) can further occur in the presence a salt. In an example, the salt can be chosen from: an ammonium salt; an alkali metal salt, such as an alkali metal halide; an alkaline-earth metal salt, such as an alkaline-earth metal halide; and combinations thereof. In some embodiments, the salt is chosen from NaCl, NaBr, KCl, $CaCl_2$, LiCl, $MgCl_2$ and LiBr.

In various embodiments, $R^1$ can be chosen from ($C_1$-$C_{20}$) alkyl, ($C_3$-$C_8$)cycloalkyl, ($C_2$-$C_{12}$)alkenyl, ($C_2$-$C_{20}$)alkynyl, ($C_6$-$C_{10}$)aryl, ($C_7$-$C_{27}$)arylalkyl, ($C_7$-$C_{27}$)alkylaryl, ($C_2$-$C_{20}$)alkylcarbonyloxy, ($C_6$-$C_{27}$)arylcarbonyloxy, ($C_2$-$C_{20}$) alkoxycarbonyl, and ($C_6$-$C_{27}$)aryloxycarbonyl groups, each of which may be substituted by one or more groups chosen from Cl, F, Br, I, R', OR', SR', NR'$_2$, SiR'$_3$, COOR', (C=O) R', CN, and CONR$_2$', wherein R' is chosen from H and ($C_1$-$C_{12}$)alkyl. In some embodiments, $R^1$ can be chosen from ($C_1$-$C_{20}$)alkyl, ($C_3$-$C_8$)cycloalkyl, ($C_2$-$C_{12}$)alkenyl, ($C_2$-$C_{20}$)alkynyl, ($C_6$-$C_{10}$)aryl, ($C_7$-$C_{27}$)arylalkyl, ($C_7$-$C_{27}$)alkylaryl, ($C_2$-$C_{20}$)alkylcarbonyloxy, ($C_6$-$C_{27}$)arylcarbonyloxy, ($C_2$-$C_{20}$) alkoxycarbonyl, and ($C_6$-$C_{27}$)aryloxycarbonyl groups.

In various embodiments. $R^2$ can be chosen from H, ($C_1$-$C_{20}$)alkyl, and ($C_6$-$C_8$)aryl groups. In some embodiments, $R^2$ can be chosen from H and phenyl.

In some embodiments the organic solvent can be chosen from 1,3-Dimethyl-3,4,5,6-tetrahydro-2(1H)-pyrimidinone, N,N-dimethylformamide and N,N-dimethylacetamide As used herein, the term "DMPU" and " 1,3-Dimethyl-3,4,5,6-tetrahydro-2(1H)-pyrimidinone," generally refers to the compound having the CAS Number 7226-23-5 having the following formula.

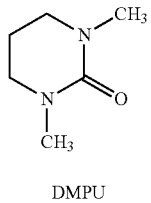

DMPU

In various embodiments, the olefin of formula (I) can be cis with respect to groups $R^1$ and $R^2$. In various embodiments, the olefin of formula (I) can be trans with respect to groups $R^1$ and $R^2$. In various embodiments, the olefin of formula (I) can be a mixture of cis and trans isomers with respect to groups $R^1$ and $R^2$. In some embodiments, the mixture can include about 75% to about 100% cis isomers with respect to groups $R^1$ and $R^2$. In some embodiments, the mixture can include about 95% to about 100% cis isomers with respect to groups $R^1$ and $R^2$. In some embodiments, the mixture can include about 75% to about 100% trans isomers with respect to groups $R^1$ and $R^2$. In some embodiments, the mixture can include about 95% to about 100% trans isomers with respect to groups $R^1$ and $R^2$.

In various embodiments, about 0.001 mol % to about 20 mol % of the palladium-based catalyst (e.g., $PdCl_2$) is used relative to the amount of compound (II). In some embodiments, about 5 mol % to about 10 mol % of the palladium-based catalyst (e.g., $PdCl_2$) can be used relative to the amount of compound (II). In some embodiments, about 0.01-19 mol %, such as about 0.1-16 mol %, for example about 1-15 mol %, such as about 2-13 mol %, for example about 3-12 mol %, such as about 4-11 mol %, for example about 0.001 mol % or less, about 0.01 mol %, about 0.1 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, or about 20 mol % or greater of the palladium-based catalyst (e.g., $PdCl_2$) is used relative to the amount of compound (II).

In various embodiments, about 10 mol % to about 200 mol % of the salt is used relative to the amount of compound (II). In some embodiments, about 95 mol % to about 105 mol % of the salt is used relative to the amount of compound (II). In some embodiments, about 100 mol % of the salt is used relative to the amount of compound (II). In some embodiments, about 55-190 mol %, for example about 60-180 mol %, such as about 65-170 mol %, for example about 70-160 mol %, such as about 75-150 mol %, for example about 80-140 mol %, such as about 85-130 mol %, for example about 90-120 mol %, such as about 95-105 mol %, for example about 50 mol % or less, about 60 mol %, about 70 mol %, about 80 mol %, about 85 mol %, about 90 mol %, about 95 mol %, about 100 mol %, about 105 mol %, about 110 mol %, about 115 mol %, about 120 mol %, about 130 mol %, about 140 mol %, about 150 mol %, about 160 mol %, about 170 mol %, about 180 mol %, about 190 mol %, or about 200 mol % or greater of the salt is used relative to the amount of compound (II).

In various embodiments, the reacting of compound (II) in the presence of the palladium-based catalyst (e.g., $PdCl_2$) and the organic solvent occurs at a temperature of about 60° C. to about 300° C. In some embodiments, the reacting of compound (II) in the presence of the palladium-based catalyst and the organic solvent occurs at a temperature of about 155° C. to about 165° C. In some embodiments, the reacting of compound (II) in the presence of the palladium-based catalyst and the organic solvent occurs at a temperature of about 160° C. In some embodiments, the reacting of compound (II) in the presence of the palladium-based catalyst and the organic solvent occurs at a temperature of about 70-280° C., for example about 80-260° C., such as about 90-240° C. for example about 100-220° C., such as about 110-210° C. for example about 120-200° C., such as about 130-190° C. for example about 140-180° C., such as about 150-170° C., for example about 60° C., about 70° C., about 80° C., about 90° C., about 100° C., about 110° C. about 120° C., about 130° C., about 140° C., about 150° C., about 160° C., about 170° C. about 180° C. about 190° C., about 200° C., about 210° C., about 220° C., about 230° C., about 240° C., about 250° C., about 260° C., about 270° C., about 280° C., about 290° C., or about 300° C., or more.

In various embodiments, the reacting of compound (II) in the presence of the palladium-based catalyst and the organic solvent occurs for about 15 min to about 36 hours. In some embodiments, the reacting of compound (II) in the presence of the palladium-based catalyst, and the organic solvent occurs for about 15 hours to about 17 hours. In some embodiments, the reacting of compound (II) in the presence of the palladium-based catalyst, and the organic solvent occurs for about 2 hours to about 4 hours. In some embodiments, the reacting of compound (II) in the presence of the palladium-based catalyst, and the organic solvent occurs for about 2-30 hours, such as about 3-24 hours, for example about 4-18 hours, such as about 1 hour or less, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, or about 36 hours or more.

Process of Catalytic Ester Decarbonylation and Tandem Heck-Type Coupling

In various embodiments, a process of preparing olefins of the formula (III) is disclosed herein.

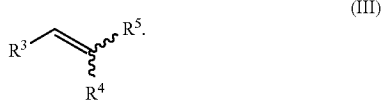

The variable $R^3$ is chosen from a substituted or unsubstituted $(C_1-C_{30})$hydrocarbyl. The variable $R^4$ is chosen from a from a substituted or unsubstituted $(C_1-C_{20})$hydrocarbyl. The variable $R^5$ is chosen from a substituted or unsubstituted $(C_1-C_{30})$hydrocarbyl. The process includes reacting a compound of formula (IV)

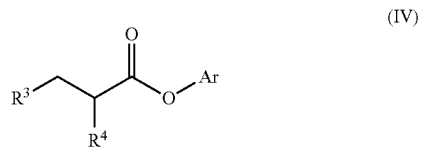

wherein $R^3$ and $R^4$ are as described above, and the variable Ar is chosen from

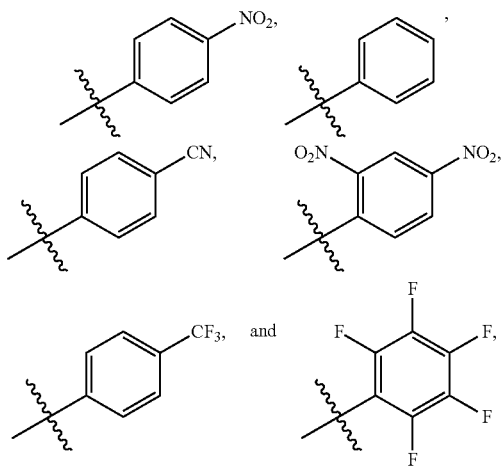

with a compound of formula (V)

in which, $R^5$ and Ar are as described above. The reacting of compound (IV) with compound (V) occurs in the presence of a catalyst, such as a palladium-based catalyst, for example $PdCl_2$, and an organic solvent. The preparation of the olefins of formula (III), as defined above, can occur in the absence of additional ligands, such as phosphine ligands.

In various embodiments, the palladium-based catalyst can be formed in situ from a palladium(0) precursor (e.g., $Pd_2(dba)_3$). In some embodiments, the palladium based catalyst can be a palladium halide (e.g., $PdCl_2$). In some embodiments, the palladium-based catalyst can be chosen from $PdCl_2$, $Pd_2(dba)_3$, $PdI_2$, $PdBr_2$ and $(COD)PdCl_2$.

In various embodiments, the reacting of the compound of formula (IV) further occurs in the presence of a salt. In an example, the salt can be chosen from: an ammonium salt; an alkali metal salt, such as an alkali metal halide; an alkaline-earth metal salt, such as an alkaline-earth metal halide; and combinations thereof. In some embodiments, the salt is chosen from NaCl, NaBr, KCl, $CaCl_2$, LiCl, $MgCl_2$ and LiBr.

In various embodiments, the variable $R^3$ can be chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$ alkoxycarbonyl, and $(C_6-C_{27})$aryloxycarbonyl groups, each of which may be substituted by one or more groups chosen from Cl, F, Br, I, R', OR', SR', NR'$_2$, SiR'$_3$, COOR', (C=O)R', CN, and CONR$_2$', wherein R' is chosen from H and $(C_1-C_{12})$alkyl. In some embodiments, the variable $R^3$ can be chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$ alkoxycarbonyl, and $(C_6-C_{27})$aryloxycarbonyl groups.

In various embodiments, the variable $R^4$ can be chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$ alkoxycarbonyl, and $(C_6-C_{27})$aryloxycarbonyl groups, each of which may be substituted by one or more groups chosen from Cl, F, Br, I, R', OR', SR', NR'$_2$, SiR'$_3$, COOR', (C=O)R', CN, and CONR$_2$', wherein $R^1$ is chosen from H and $(C_1-C_{12})$alkyl. In some embodiments, the variable $R^4$ is chosen from H and phenyl.

In various embodiments, $R^5$ can be chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$ alkoxycarbonyl, and $(C_6-C_{27})$aryloxycarbonyl groups, each of which may be substituted by one or more groups chosen from Cl, F, Br, I, R', OR', SR', NR'$_2$, SiR'$_3$, COOR', (C=O) R', CN, and CONR$_2$', wherein R' is chosen from H and $(C_1-C_{12})$alkyl. In some embodiments, the variable $R^5$ can be chosen from $(C_6-C_{10})$aryl, $(C_7-C_{27})$arylalkyl, $(C_7-C_{27})$alkenylaryl groups. In some embodiments, the variable $R^5$ can be chosen from

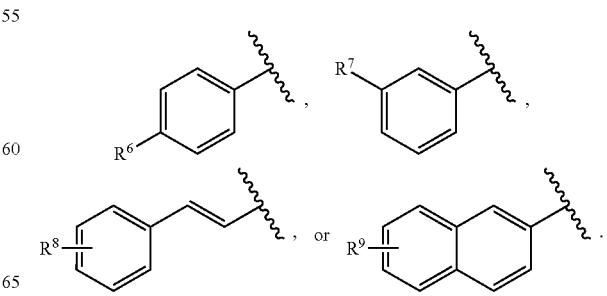

The variables $R^6$, $R^7$, $R^8$, and $R^9$ can each independently chosen from H, Cl, Br, F, $NO_2$, OH, OR' and $(C_1-C_5)$alkyl. The variable R' can be a $(C_1-C_5)$alkyl.

In various embodiments, the salt can be an alkali metal halide, an alkaline-earth metal halide, and combinations thereof. For example, the salt can be one or more of NaCl, NaBr, KCl, $CaCl_2$, LiCl, $MgCl_2$ and LiBr. In some embodiments, the salt is tetrabutylammonium bromide.

In some embodiments, the organic solvent can be chosen from 1,3-Dimethyl-3,4,5,6-tetrahydro-2(1H)-pyrimidinone. N,N-dimethylformamide and N,N-dimethylacetamide.

In various embodiments, the olefin of formula (III) can be cis with respect to groups $R^3$ and $R^5$. In various embodiments, the olefin of formula (III) can be trans with respect to groups $R^3$ and $R^5$. In various embodiments, the olefin of formula (III) can be a mixture of cis and trans isomers with respect to groups $R^3$ and $R^5$. In some embodiments, the mixture can include about 75% to about 100% cis isomers with respect to groups $R^3$ and $R^5$. In some embodiments, the mixture can include about 95% to about 100% cis isomers with respect to groups $R^3$ and $R^5$. In some embodiments, the mixture can include about 75% to about 100% trans isomers with respect to groups $R^3$ and $R^5$. In some embodiments, the mixture can include about 95% to about 100% trans isomers with respect to groups $R^3$ and $R^5$.

In various embodiments, about 0.001 mol % to about 20 mol % of the palladium-based catalyst (e.g., $PdCl_2$) can be used relative to the amount of compound (IV). In some embodiments, about 5 mol % to about 10 mol % of the palladium-based catalyst can be used relative to the amount of compound (IV). In some embodiments, about 0.01-19 mol %, such as about 0.1-16 mol %, for example about 1-15 mol %, such as about 2-13 mol %, for example about 3-12 mol %, such as about 4-11 mol %, for example about 0.001 mol % or less, about 0.01 mol %, about 0.1 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, or about 20 mol % or greater of the palladium-based catalyst can be used relative to the amount of compound (IV).

In various embodiments, about 10 mol % to about 200 mol % of the salt can be used relative to the amount of compound (IV). In some embodiments, about 95 mol % to about 105 mol % of the salt can be used relative to the amount of compound (IV). In some embodiments, about 100 mol % of the salt can be used relative to the amount of compound (IV). In some embodiments, about 55-190 mol %, such as about 60-180 mol %, for example about 65-170 mol %, such as about 70-160 mol %, for example about 75-150 mol %, such as about 80-140 mol %, for example about 85-130 mol %, such as about 90-120 mol %, for example about 95-105 mol %, such as about 50 mol % or less, about 60 mol %, about 70 mol %, about 80 mol %, about 85 mol %, about 90 mol %, about 95 mol %, about 100 mol %, 105 mol %, 110 mol %, 115 mol %, 120 mol %, 130 mol %, 140 mol %, 150 mol %, 160 mol %, 170 mol %, 180 mol %, 190 mol %, or about 200 mol % or greater of the salt can be used relative to the amount of compound (IV).

In various embodiments, the reacting of compound (IV) with compound (V) in the presence of the palladium-based catalyst (e.g., $PdCl_2$) and the organic solvent occurs at a temperature of about 60° C. to about 300° C. In some embodiments, the reacting of compound (IV) with compound (V) in the presence of the palladium-based catalyst and the organic solvent occurs at a temperature of about 155° C. to about 165° C. In some embodiments, the reacting of compound (IV) with compound (V) in the presence of the palladium-based catalyst and the organic solvent occurs at a temperature of about 160° C. In some embodiments, the reacting of compound (IV) with compound (V) in the presence of the palladium-based catalyst and the organic solvent occurs at a temperature of about 70-280° C., for example about 80-260° C. such as about 90-240° C. for example about 100-220° C., such as about 110-210° C., for example about 120-200° C., such as about 130-190° C., for example about 140-180° C., such as about 150-170° C., for example about 60° C. about 70° C., about 80° C., about 90° C., about 100° C., about 110° C., about 120° C., about 130° C., about 140° C., about 150° C. about 160° C. about 170° C., about 180° C., about 190° C. about 200° C. about 210° C., about 220° C., about 230° C., about 240° C. about 250° C. about 260° C., about 270° C., about 280° C., about 290° C., or about 300° C. or more.

In various embodiments, the reacting of compound (IV) with compound (V) in the presence of the palladium-based catalyst and the organic solvent occurs for about 1 hour to about 36 hours. In various embodiments, the reacting of compound (IV) with compound (V) in the presence of the palladium-based catalyst and the organic solvent occurs for about 15 hours to about 17 hours. In some embodiments, wherein the reacting of compound (IV) with compound (V) in the presence of the palladium-based catalyst and the organic solvent occurs for about 2 hours to about 4 hours. In some embodiments, the reacting of compound (IV) with compound (V) in the presence of the palladium-based catalyst, and the organic solvent occurs for about 2-30 hours, 3-24 hours, or about 4-18 hours, for example 1 hour or less, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, or about 36 hours or more.

Reaction Selection to α-Olefin Products with One or More Selection-Enhancing Ligands The decarbonylation reactions described herein (e.g., preparing olefins of the formula (I) by reacting compounds of formula (II), or preparing olefins of the formula (III) via the tandem Heck-type coupling reaction of the compound of formula (IV) with the compound of the formula (V)) can produce olefins with moderate to good yields. However, it has been found by the inventors that the reaction conditions for the reactions described above can result in relatively high olefin isomerization that can produce a statistical mixture of olefinic products. The mixture of a relatively large number of olefin isomers can be undesirable because it can require additional separation steps to yield the olefin or olefins of interest for a particular application. In addition, it has been found that in some examples, this isomerization can make it difficult to achieve a high reaction yield of terminal olefin products, also referred to herein as α-olefin products, such as linear α-olefin products or "LAO products." As used herein, the terms "terminal olefin" or "α-olefin" can refer to an olefin wherein the double bond is formed at a terminal carbon, or a carbon, in the chain (sometimes also called the primary carbon). i.e., such that one of the carbon atoms that forms the double bond is at an end of the carbon chain and has two attached hydrogen atoms or a non-carbon hydrogen substitution (e.g., a halide). For example, a linear olefin comprising eight carbon atoms, referred to as octene, can be considered a terminal olefin or α-olefin within the meaning of this disclosure if a double bond is formed between the first carbon atom and the second carbon atom or between the seventh carbon atom and the eighth carbon atom.

LAOs are valuable commodity chemicals because they find widespread applications as comonomers in polyethylene production, in surfactants, linear alkylbenzene sulphonates, low molecular weight polymers, and the like. For example, decarbonylation of nonanoic acid ester via the decarbonylation reactions described above (e.g., in the presence of a catalyst. e.g., a palladium-based catalyst, and a solvent, and in some embodiments in the presence of a salt) has been found, in some examples, to produce a mixture of octene isomers with only 14% 1-octene present therein, wherein 1-octene is the LAO produced by decarbonylation of nonanoic acid.

Previously, LAOs have been produced by ethylene oligomerization or Fischer-Tropsch process, which use petroleum as feedstock. Conversely, fatty acids, obtainable from animal fats and vegetable oils, can be converted to LAOs by decarbonylation. Moreover, since fatty acids can comprise an even number of carbon atoms, decarbonylation can generate α-olefins with an odd-carbon number and hence, can provide access to chemical feedstock that is complementary to those derived from petrochemical sources.

In order to render the decarbonylation reaction described above (e.g., decarbonylation of a compound of formula (II)) selective for an α-olefin product, and in particular for a linear α-olefin (LAO) product, the effect of certain added ligands on decarbonylation was investigated. As described in more detail below, it has been found by the inventors that the addition of certain ligands to the reaction mixture can improve selectivity toward LAO products, for example to a selectivity to an LAO of at least 50%, for example at least 55%, at least 60%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, or at least 80% or greater. In an example, described in more detail below, the addition of a particular ligand to the reaction mixture for the decarbonylation of p-nitrophenylnonanoate (e.g., the p-nitrophenol ester of nonanoic acid) to 1-octene, the selectivity was as high as 82%, with a conversion of greater than 95%.

The ligand used for reaction selection to an α-olefin product, such as a LAO product, can be a phosphine-based ligand. As used herein, the term "phosphine" can refer to organophosphorus compounds that are alkyl and aryl derivatives of phosphine ($PH_3$). e.g., with one or more of the hydrogen atoms of phosphine being replaced by one or more alkyl or aryl groups. In an example, a phosphine-based ligand can be a phenylphosphine-based ligand, e.g., a phosphine comprising a group made up of one or more phenyl rings bonded to a phosphorus atom. In some examples, the phenylphosphine-based ligand comprises a group made up of two or more phenyl rings bonded to a phosphorus atom, such as a compound with one or more diphenylphosphine groups (—$PPh_2$), or a triphenylphosphine ($PPh_3$) ligand. Specific organophosphorus phosphines that can be used as a ligands for the selective formation of α-olefins, such as LAOs, from decarbonylation include, but are not limited to, one or more of triphenylphosphine ($P(C_6H_5)_3$, commonly abbreviated as "$PPh_3$"), bis-[2-(diphenylphosphino)phenyl] ether ($O[C_6H_4P(C_6H_5)_2]_2$, commonly abbreviated as "DPEphos"), and 4,5-Bis(diphenylphosphine)-9,9-dimethylxanthene ($C_{39}H_{32}OP_2$, commonly abbreviated as "Xantphos"). In some examples, Xantphos has been found to be particularly effective as a ligand for selective reaction to LAO products. Other classes of ligands can be usable as well. In some examples, a heterocyclic carbene ligand can be used, such as a N-heterocyclic carbene ligand, such as d 1,3-bis(2,6-diisopropylphenyl)imidazol-2-ylidene (commonly abbreviated as "IPr") or 1,3-bis(2,4,6-trimethylphenyl)imidazol-2-ylidene (commonly abbreviated as "IMes"). In some examples, a combination of one or more organophosphorus phosphine ligands, such as one or more phenylphosphine-based ligands, for example Xantphos, and one or more heterocyclic carbene ligands, such as one or more N-heterocyclic carbene ligands, such as IPr, can be used for the selective reaction to one or more α-olefin products.

The one or more ligands being used for selective reaction to an α-olefin product can be added to the reaction mixture at a concentration that is sufficient to render the reaction to the desired α-olefin product. In an example, the molar percentage of the one or more ligands in the reaction mixture can be at least about 5%, such as at least about 10%, for example at least about 20%. The molar concentration used can depend on the specific ligand or ligands being used as well as the reactants. In an example with Xantphos as the ligand, a molar concentration of about 5% for the Xantphos was found to be sufficient for selectivity to a desired α-olefin product of as high as 82%. In an example with a combination of one or more organophosphorus phosphine ligands, such as one or more phenylphosphine-based ligands, for example Xantphos, and one or more heterocyclic carbene ligands, such as one or more N-heterocyclic carbene ligands, for example IPr, each type of ligand can have a molar percentage in the reaction mixture of at least 5%, for example with Xantphos being at least about 5 mol % and IPr also being at least about 5 mol %.

The selectivity toward the one or more desired α-olefin products can also depend on other factors, such as reaction temperature. In an example, a higher temperature can be desired to achieve an acceptable selectivity toward the desired one or more α-olefin products and an acceptable conversion of the reactants. In an example, the reaction temperature can be greater than about 160° C., for example at least 170° C., such as at least 180° C., for example around 190° C. The reaction temperature chosen can depend on the one or more ligands being used and the molar concentration of those one or more ligands.

The use of the one or more ligands described herein for the selective decarbonylation of fatty acid esters to one or more α-olefin products, such as one or more linear α-olefin products, is believed to be a unique reaction scheme. Current literature on selective decarbonylation of fatty acids involves the use of carboxylic acid anhydrides as substrates, which in turn are generated from the corresponding fatty acids and a sacrificial anhydride.

EXAMPLES

Various embodiments of the present invention can be better understood by reference to the following Examples which are offered by way of illustration. The present invention is not limited to the Examples given herein.

Example 1

Screening of Ni and Pd Catalysts for the Decarbonylation of p-Nitrophenylester of Hydrocinnamic Acid Initial test reactions focused on screening the decarbonylation of the p-nitrophenylester of hydrocinnamic acid using various Ni and Pd catalysts (e.g., NiI$_2$, Ni(COD)$_2$, PdCl$_2$, PdI$_2$) in the presence of phosphine ligands. e.g., PPh$_3$, PCy$_3$, Bis[(2-diphenylphosphino)phenyl]ether, diphenylphosphinoethane, dicyclohexylphosphinoethane, and diphenylphosphinobutane. Irrespective of the conditions employed, the reactions yielded only ~5-10% styrene and almost quantitative ester hydrolysis was noted.

Example 2

Effects of Salts on the Decarbonylation Reaction

Experiments were conducted to determine the effect of salts on the decarbonylation reaction according to the following scheme, with results presented in Table 1.

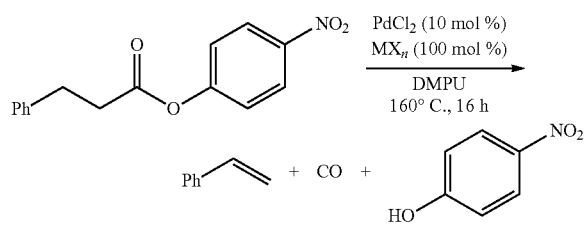

TABLE 1

Effect of salts on the decarbonylation reaction.[a]

| entry | MX$_n$ | yield (%)[b] |
|---|---|---|
| 1 | — | 46 |
| 2 | NaCl | 51 |
| 3 | NaBr | 58 |
| 4 | KCl | 52 |
| 5 | CH$_3$COONa | <5 |
| 6 | TBAB | 62 |
| 7 | CaCl$_2$ | 71 |
| 8 | LiCl | 78 |
| 9 | MgCl$_2$ | 53 |
| 10 | LiBr | 66 |

[a]Reaction conditions: p-nitrophenylhydrocinnamate (0.075 g, 0.276 mmol), PdCl$_2$ (0.004 g, 0.023 mmol, 10 mol %) and metal halide (0.263 mmol) in DMPU (ca. 0.5 mL) at 160° C. for 16 hours.
[b]Determined by GC using 1,3,5-trimethoxybenzene as internal standard.

The yield dropped to 54% when its loading was reduced to 20 mol % (Table 2, entry 2) as compared to 79% when the loading was 100% (Table 2, entry 1). The reaction temperature also was found to have significant effect on the reaction efficiency (entries 4 and 5; 27% yield at 120° C. over 16 h vs, 67% yield at 140° C. in 3 h). Loadings of PdCl$_2$ of 2.5 mol % and 1 mol % resulted in only modest decreases in product yield (entries 3 and 7). Addition of N-donor ligands (pyridine, DMAP) had a detrimental effect (entry 6; styrene yield <5%). Through these combined studies, optimal conditions were identified as PdCl$_2$ (2.5 mol %), LiCl (100%) in DMPU (about 0.5 mL) at 160° C. for 3 h (Table 2, entry 3).

Representative procedure for decarbonylation reactions. Inside a N$_2$ filled glove box, a Schlenk tube was charged with the p-nitrophenylhydrocinnamate (0.075 g, 0.276 mmol, 1 equiv.), PdCl$_2$ (0.004 g, 0.026 mmol, 10 mol % or 0.002 g, 0.013 mmol, 5 mol %). LiCl (0.010 g, 0.236 mmol, 100 mol %) and DMPU (ca. 0.5 mL) was injected in followed by a Teflon-coated stir bar to yield a light yellow mixture. The Schlenk tube was sealed, brought outside the glove box and set in an oil bath pre-heated to 155-160° C. The reaction mixture was allowed to stir at this temperature for the stipulated period of time during which it darkened to a final red-brown color. At the end of the reaction, the Schlenk tube was removed from the oil bath and allowed to cool to room temperature. (a) For GC-MS analysis: The reaction mixture was transferred to a separatory funnel diluted with EtOAc (ca. 5 mL) and washed with 1M HCl (ca. 5 mL×2) and brine (ca. 5 mL). The organic layer was collected, dried over MgSO$_4$, and analyzed by GC-MS using 1,3,5-trimethoxybenzene as an internal standard. (b) For olefin isolation (reaction carried out at 1 mmol scale): The reaction mixture was transferred to a separatory funnel, diluted with 1M HCl (ca. 10 mL). This mixture was extracted with pentane (ca. 5 ml×3). The combined organic layers were washed with 1M HCl (ca. 5 mL) and then separated. The pentane extracts were dried with MgSO$_4$, and then concentrated under vacuum to remove the pentane. Analysis of the residue by $^1$H NMR spectroscopy showed the olefin product in >90% purity.

Example 3

Effect of Time and Temperature on the Decarbonylation of p-Nitrophenylhydrocinnamate Experiments were conducted to determine the effect of time and temperature on the decarbonylation of p-nitrophenylhydrocinnamate, with results presented in Table 2.

TABLE 2

Decarbonylation of p-nitrophenylhydrocinnamate.[a]

| entry | conversion (%) | T (° C.) | time (h) | yield (%)[b] |
|---|---|---|---|---|
| 1[c] | | 160 | 16 | 79 |
| 2[d] | | 160 | 16 | 54 |
| 3[e] | | 160 | 3 | 75 |
| 4 | 65 | 120 | 16 | 27 |
| 5 | | 140 | 3 | 67 |
| 6[f] | 45 | 140 | 3 | <5 |
| 7[g] | 94 | 160 | 5 | 47 |

[a]Reaction conditions: p-nitrophenylhydrocinnamate (0.075 g, 0.276 mmol), PdCl$_2$ (0.004 g, 0.023 mmol, 5 mol %) and LiCl (0.010 g, 0.236 mmol, 100 mol %) in DMPU (ca. 0.5 mL).
[b]Determined by GC using 1,3,5-trimethoxybenzene as internal standard.
[c]PdCl$_2$ (5 mol %).
[d]LiCl (20 mol %).
[e]PdCl$_2$ (2.5 mol %).
[f]pyridine (50%).
[g]PdCl$_2$ (1 mol %).

Example 4

Decarbonylation of p-Nitrophenylesters

Experiments were conducted into the decarbonylation of p-nitrophenylesters, with results presented in Table 3.

TABLE 3

Substrate scope for decarbonylation of p-nitrophenylesters.[a]

| entry | acid | olefin | yield[b] (%) |
|---|---|---|---|
| 1. | Ph~~~C(O)O-Ar | Ph~~~ | 53 (79) |

TABLE 3-continued

Substrate scope for decarbonylation of p-nitrophenylesters.[a]

| entry | acid | olefin | yield[b] (%) |
|---|---|---|---|
| 2. | 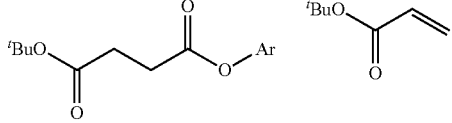 | 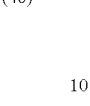 | (46) |
| 3. | 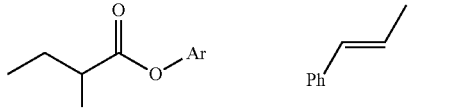 | 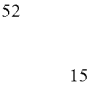 | 52 |
| 4. | 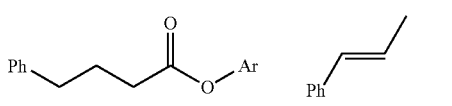 | 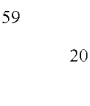 | 59 |
| 5. | 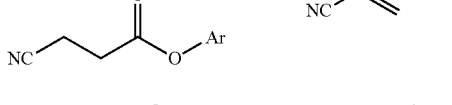 | 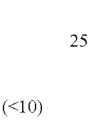 | (44) |
| 6. | 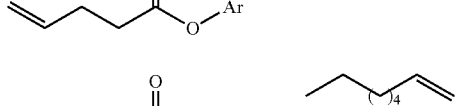 | 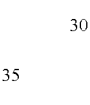 | (<10) |
| 7.[c] | 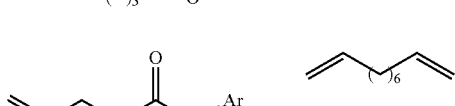 | 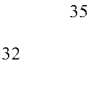 octene isomers | 35 |
| 8.[c] | 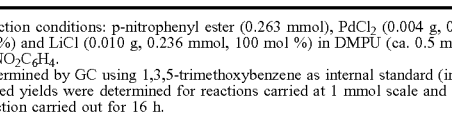 | 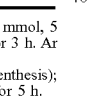 decene isomers | 32 |

[a]Reaction conditions: p-nitrophenyl ester (0.263 mmol), PdCl$_2$ (0.004 g, 0.023 mmol, 5 mol %) and LiCl (0.010 g, 0.236 mmol, 100 mol %) in DMPU (ca. 0.5 mL) for 3 h. Ar = p-NO$_2$C$_6$H$_4$.
[b]Determined by GC using 1,3,5-trimethoxybenzene as internal standard (in parenthesis); isolated yields were determined for reactions carried at 1 mmol scale and run for 5 h.
[c]Reaction carried out for 16 h.

Example 5

Tandem Decarbonylation Heck-Coupling Decarbonylation

A series of experiments were conducted to investigate the decarbonylation reaction with a decarbonylative Heck-type coupling reaction in (Scheme Table [1]; shown below), with results presented in Table 4. Starting from equivalent amounts of p-nitrophenylbenzoate and p-nitrophenolhydrocinnmate, trans-stilbene was produced in 61% yield under our optimized reaction conditions. This first demonstration of the use of a carboxylic acid ester as a "masked olefin" in a Heck-coupling reaction has intriguing potential as a tool in synthesis. Monitoring of the progress of the tandem Heck-coupling reaction by GC-MS analysis showed initial buildup of styrene and loss of the hydrocinnamic ester in the mixture prior to trans-stilbene generation accompanied by styrene and benzoate ester consumption FIG. 1. Substituted benzoic acid esters participated in the reaction to yield the respective asymmetric stilbenes, consistent with cross-coupling of components from the two different ester starting materials. The cross-coupling efficiency decreased when activated aromatic esters (with electron withdrawing substituents) were used, as their decarbonylation to yield the corresponding parent arene via protonation of the Ar—Pd intermediate was competitive. When p-nitrophenol-4-bromobenzoate was employed as the coupling partner, a minor amount of trans-stilbene (<5%) was observed in the reaction mixture along with 4-bromostilbene, presumably arising from the coupling of styrene with bromobenzene.

Scheme [1]

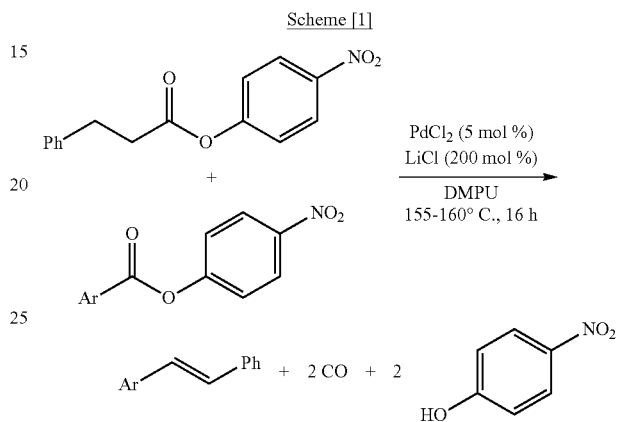

TABLE 4

Tandem Decarbonylation Heck-coupling decarbonylation[a]

| entry | Ar | yield[b] (%) |
|---|---|---|
| 1. | C$_6$H$_5$— | 61 |
| 2. | m-ClC$_6$H$_4$— | 42 |
| 3. | p-MeC$_6$H$_4$— | 25 |
| 4. | p-NO$_2$C$_6$H$_4$— | 13 |
| 5. | p-BrC$_6$H$_4$— | 11 |
| 6. | C$_6$H$_5$CH=CH$_2$— | 28 |
| 7. | 2-Naphthyl- | 40 |

[a]Reaction conditions: p-nitrophenylhydrocinnamate (0.071 g, 0.26 mmol), p-nitrophenylbenzoate (0.26 mmol), PdCl$_2$ (0.002 g, 0.013 mmol, 5 mol %) and LiCl (0.020 g, 0.47 mmol, 200 mol %) in DMPU (ca. 0.5 mL) for 16 hours.
[b]Isolated yields.

A procedure for tandem Heck-coupling reaction was performed. Inside a N$_2$ filled glove box, a Schleck tube was charged with the p-nitrophenylhydrocinnamate (0.071 g, 0.262 mmol, 1 equiv.), p-nitrophenylbenzoate (0.064 g, 0.262 mmol, 1 equiv.), PdCl$_2$ (0.002 g, 0.013 mmol, 5 mol %), LiCl (0.020 g, 0.472 mmol, 200 mol %) and DMPU (ca. 0.5 mL) was injected in followed by a Teflon-coated stir bar. The sealed Schleck tube was brought outside and placed in an oil bath preheated to 155-160° C. and allowed to stir at this temperature for 16 hours. At the end of this period, the reaction mixture was allowed to cool to room temperature and then diluted with EtOAc (ca. 5 mL). The solution was transferred to a separatory funnel and washed with 1M HCl (ca. 5 mL×2) followed by brine solution (ca. 5 mL). The organic layer was separated, dried over MgSO$_4$, filtered and then analyzed by GC-MS using 1,3,5-trimethoxybenzene as an internal standard. For isolation of the product, a procedure similar to that used for olefin isolation was employed using pentane as the organic solvent.

trans-stilbene (Entry 1)

$^1$H NMR (CDCl$_3$, 300 MHz, 25° C.): δ 7.52 (d, $^3J_{HH}$=8.7 Hz, 4H), 7.37 (t, $^3J_{HH}$=7.5 Hz, 4H), 7.26 (t, $^3J_{HH}$=7.5 Hz, 2H), 7.12 (s, 2H).

3-chlorostilbene (Entry 2)

$^1$H NMR (CDCl$_3$, 300 MHz, 25° C.): δ 7.53-7.51 (m, 3H), 7.41-7.36 (m, 3H), 7.29 (t, $^3J_{HH}$=7.5 Hz, 2H), 7.26-7.22 (m, 1H), 7.12 (d, $^3J_{HH}$=16 Hz, 1H), 7.03 (d, $^3J_{HH}$=16 Hz, 1H).

4-methylstilbene (Entry 3)

$^1$H NMR (CDCl$_3$, 300 MHz, 25° C.): δ 7.52 (d, $^3J_{HH}$=7.5 Hz, 2H), 7.44-7.34 (m, 4H), 7.28-7.23 (m, 1H), 7.18 (d, $^3J_{HH}$=7.8 Hz, 2H), 7.09 (s, 2H), 2.37 (s, 3H).

4-nitrostilbene (Entry 4)

$^1$H NMR (CDCl$_3$, 300 MHz, 25° C.): δ 8.23 (d, $^3J_{HH}$=8.7 Hz, 2H), 7.65 (d, $^3J_{HH}$=8.7 Hz, 2H), 7.56 (d, $^3J_{HH}$=6.9 Hz, 2H), 7.41 (t, $^3J_{HH}$=6.9 Hz, 2H), 7.37-7.32 (m, 1H), 7.26-7.31 (m, 1H), 7.15 (d, $^3J_{HH}$=16 Hz, 1H).

4-bromostilbene (Entry 5)

$^1$H NMR (CDCl$_3$, 500 MHz, 25° C.): δ 7.54-7.48 (m, 4H), 7.40-7.36 (m, 4H), 7.29 (t, $^3J_{HH}$=6.5 Hz, 1H), 7.10 (d, $^3J_{HH}$=16 Hz, 1H), 7.04 (d, $^3J_{HH}$=16 Hz, 1H).

1,4-diphenyl-1,3-butadiene (Entry 6)

$^1$H NMR (CDCl$_3$, 500 MHz, 25° C.): δ 7.45 (d, $^3J_{HH}$=7 Hz, 4H), 7.34 (t, $^3J_{HH}$=7.5 Hz, 4H), 7.24 (t, $^3J_{HH}$=7.0 Hz, 2H), 7.00-6.94 (m, 2H), 6.72-6.66 (m, 2H).

2-styrylnaphthalene (Entry 7)

$^1$H NMR (CDCl$_3$, 500 MHz, 25° C.): δ 7.88 (s, 1H), 7.86-7.82 (m, 3H), 7.77 (dd, $^3J_{HH}$=9.0 Hz & $^3J_{HH}$=2.0 Hz, 1H), 7.58 (d, $^3J_{HH}$=7.5 Hz, 2H), 7.51-7.45 (m, 2H), 7.40 (d, $^3J_{HH}$=8.0 Hz, 2H), 7.32-7.24 (m, 3H).

Example 6

Investigation of Potential Selection-Enhancing Ligands for Selective Decarbonylation to α-Olefin Products The p-nitrophenol ester of nonanoic acid was subjected to decarbonylation in the presence of a PdCl$_2$ catalyst in DMPU solvent to form 1-octane. LiCl salt and various ligands were also added to the reaction mixture, as indicated by Scheme [2].

Scheme [2]

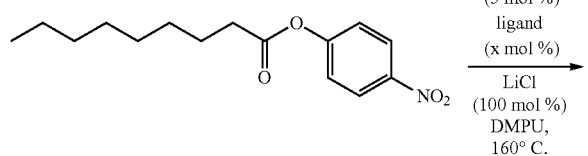

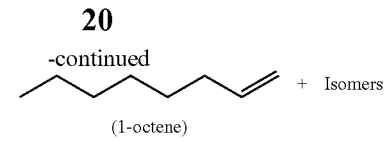

(1-octene)

Several different ligands at different molar concentrations and reaction temperatures were investigated, identified as trials 6A-6L in Table 4.

TABLE 5

Effect of Different Ligands on Decarbonylation of the p-nitrophenylnonanoate

| Trial | Ligand (mol %) | T (° C.) | Conversion$^a$ (%) | Selectivity$^b$ (1-octene %) |
|---|---|---|---|---|
| 6A$^c$ | — | 160 | >95 | 14 |
| 6B$^d$ | — | 160 | >95 | 14 |
| 6C | dba (10%) | 160 | <20 | 15 |
| 6D | N-Cbz-L-alanine (10%) | 160 | <20 | 15 |
| 6E | IPr (10%) | 160 | <20 | 20 |
| 6F | PPh$_3$ (10%) | 160 | <20 | 33 |
| 6G | PPh$_3$ (20%) | 160 | <20 | 61 |
| 6H | DPEphos (5%) | 160 | <20 | 70 |
| 6I | PPh$_3$ (20%) | 190 | >95 | 46 |
| 6J | DPEphos (5%) | 190 | >95 | 35 |
| 6K | DPEphos (10%) | 190 | >95 | 45 |
| 6L | Xantphos (5%) | 190 | >95 | 82 |

$^a$Determined by GCMS.
$^b$Determined by GCMS, 1-octene vs sum of internal octenes.
$^c$Reaction carried out in a closed reactor over 16 h.
$^d$Reaction carried out in a continuous distillation mode for 16 h.

As demonstrated in Table 5, it was found that the addition of Xantphos improved the selectivity significantly (~80% 1-octene).

Example 7

Investigation of Potential Selection-Enhancing Ligands for Selective Decarbonylation to α-Olefin Products A combination of Xantphos and IPr was used as ligands for decarbonylation of p-nitrophenol esters of various fatty acids according to Scheme [3].

Scheme [3]

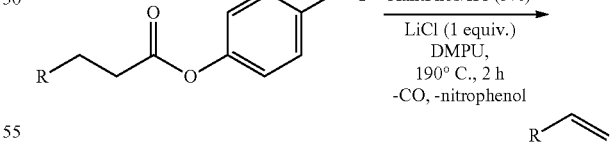

For each reaction, the fatty acid ester was fed at a concentration of 0.449 mmol. A PdCl$_2$ catalyst was introduced to the reaction mixture at 2.5 mol. %. Each of the Xantphos and IPr ligands were at 5 mol. % in the reaction mixture. One equivalent of LiCl with respect to the fatty acid ester was also added to the reaction mixture, e.g., 0.449 mmol. Each reaction mixture was heated to 190° C., and held for 2.5 hours. For each fatty acid ester investigated, the conversion was approximately 90%. Table 6 shows results of trials for the p-nitrophenol ester of various fatty acids.

TABLE 6

Conversion of p-nitrophenol esters of various fatty acids using Xantphos and IPr as selectivity-enhancing ligands

| Trial | Fatty Acid | α-olefin product | α-olefin Selectivity[a] (%) |
|---|---|---|---|
| 7A | 4-phenylbutyric | allybenzene | >98 |
| 7B | Nonanoic | 1-octene | >98 |
| 7C | Undecylenic | 1,9-decadiene | >98 |
| 7D | Lauric | 1-undecene | >98 |
| 7E | Myristic | 1-tridecene | >98 |
| 7F | Palmitic | 1-pentadecene | >98 |
| 7G | Stearic | 1-heptadecene | >98 |
| 7H | Oleic | 1,9(Z)-heptadecadiene | 71 |

[a]Determined by GCMS and $^1$H NMR analysis.

As shown in Table 6, the combination of Xantphos and IPr was found to yield greater than 98% pure α-olefin with a variety of fatty acid esters with a reaction time of about 2 hours. The conversion of the ester was about 90% after this time. Isolated yield of 1-octene from a reaction conducted at 2 mmol scale was 62%.

The terms and expressions that have been employed are used as terms of description and not of limitation, and there is no intention in the use of such terms and expressions of excluding any equivalents of the features shown and described or portions thereof, but it is recognized that various modifications are possible. Thus, it should be understood that although specific embodiments are described herein with reference to optional features, modification and variation of the concepts described herein may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides for a process of preparing olefins of the formula (I):

(I)

wherein:

R$^1$ is chosen from a substituted or unsubstituted (C$_1$-C$_{30}$) hydrocarbyl;

R$^2$ is chosen from a substituted or unsubstituted (C$_1$-C$_{20}$) hydrocarbyl;

the process comprising:

reacting a compound of formula (II)

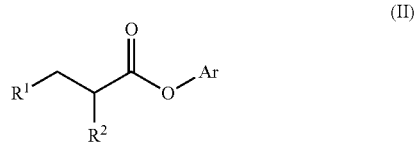

(II)

wherein Ar is chosen from

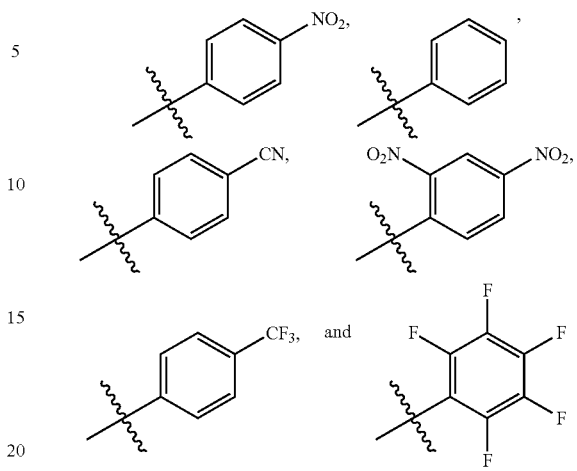

in the presence of a palladium-based catalyst, and an organic solvent, to provide the compound of formula (I).

Embodiment 2 provides for the process of Embodiment 1, wherein the preparation of the olefins of formula (I), as defined above, occurs in the absence of a phosphine ligand.

Embodiment 3 provides for the process of either one of Embodiments 1 or 2, wherein the palladium-based catalyst is formed in situ from a palladium(0) precursor.

Embodiment 4 provides for the process of anyone of embodiments 1-3, wherein the palladium-based catalyst is a palladium halide.

Embodiment 5 provides for the process for any one of Embodiments 1-4 wherein the palladium-based catalyst is PdCl$_2$ is chosen from PdCl$_2$. Pd$_2$(dba)$_3$, PdI$_2$, PdBr$_2$ and (COD)PdCl$_2$.

Embodiment 6 provides for the process of any one of Embodiments 1-5, wherein the reacting of the compound of formula (II) further occurs in the presence a salt.

Embodiment 7 provides for the process of any one of Embodiments 1-6, wherein the salt is chosen from an alkali metal halide, an alkaline-earth metal halide, and combinations thereof.

Embodiment 8 provides for the process of any one of Embodiments 1-7, wherein the salt is chosen from NaCl, NaBr, KCl, CaCl$_2$, LiCl, MgCl$_2$ and LiBr.

Embodiment 9 provides for the process of any one of Embodiments 1-8, wherein the salt is tetrabutylammonium bromide.

Embodiment 10 provides for the process of any one of Embodiments 1-9, wherein R$^1$ is chosen from (C$_1$-C$_{20}$)alkyl, (C$_3$-C$_8$)cycloalkyl, (C$_2$-C$_{12}$)alkenyl, (C$_2$-C$_{20}$)alkynyl, (C$_6$-C$_{10}$)aryl, (C$_7$-C$_{27}$)arylalkyl, (C$_7$-C$_{27}$)alkylaryl, (C$_2$-C$_{20}$)alkylcarbonyloxy, (C$_6$-C$_{27}$)arylcarbonyloxy, (C$_2$-C$_{20}$)alkoxycarbonyl, and (C$_6$-C$_{27}$)aryloxycarbonyl groups, each of which may be substituted by one or more groups chosen from Cl, F, Br, I, R', OR', SR', NR'$_2$, SiR'$_3$, COOR', (C=O)R', CN, and CONR$_2$', wherein R' is chosen from H and (C$_1$-C$_{12}$)alkyl.

Embodiment 11 provides for the process of any one of Embodiments 1-10, wherein R$^1$ is chosen from (C$_1$-C$_{20}$) alkyl, (C$_3$-C$_8$)cycloalkyl, (C$_2$-C$_{12}$)alkenyl, (C$_2$-C$_{20}$)alkynyl, (C$_6$-C$_{10}$)aryl, (C$_7$-C$_{27}$)arylalkyl, (C$_7$-C$_{27}$)alkylaryl, (C$_2$-C$_{20}$)alkylcarbonyloxy, (C$_6$-C$_{27}$)arylcarbonyloxy, (C$_2$-C$_{20}$)alkoxycarbonyl, and (C$_6$-C$_{27}$)aryloxycarbonyl groups.

Embodiment 12 provides for the process of any one of Embodiments 1-11, wherein $R^2$ is chosen from H, $(C_1$-$C_{20})$ alkyl, and $(C_6$-$C_8)$aryl.

Embodiment 13 provides for the process of any one of Embodiments 1-12, wherein the organic solvent is chosen from 1,3-Dimethyl-3,4,5,6-tetrahydro-2(1H)-pyrimidinone, N,N-dimethylformamide and N,N-dimethylacetamide.

Embodiment 14 provides for the process of any one of Embodiments 1-13, $R^2$ is chosen from H and phenyl.

Embodiment 15 provides for the process of any one of Embodiments 1-14, wherein the olefin of formula (I) is cis with respect to groups $R^1$ and $R^2$.

Embodiment 16 provides for the process of any one of Embodiments 1-15, wherein the olefin of formula (I) is trans with respect to groups $R^1$ and $R^2$.

Embodiment 17 provides for the process of any one of Embodiments 1-16, wherein the olefin of formula (I) is a mixture of cis and trans isomers with respect to groups $R^1$ and $R^2$.

Embodiment 18 provides for the process of any one of Embodiments 1-17, wherein the mixture comprises about 75% to about 100% cis isomers with respect to groups $R^1$ and $R^2$.

Embodiment 19 provides for the process of any one of Embodiments 1-18, wherein the mixture comprises about 95% to about 100% cis isomers with respect to groups $R^1$ and $R^2$.

Embodiment 20 provides for the process of any one of Embodiments 1-19, wherein the mixture comprises about 75% to about 100% trans isomers with respect to groups $R^1$ and $R^2$.

Embodiment 21 provides for the process of any one of Embodiments 1-20, wherein the mixture comprises about 95% to about 100% trans isomers with respect to groups $R^1$ and $R^2$.

Embodiment 22 provides for the process of any one of Embodiments 1-21, wherein about 0.001 mol % to about 20 mol % of the catalyst is used relative to the amount of compound (II).

Embodiment 23 provides for the process of any one of Embodiments 1-22, wherein about 5 mol % to about 10 mol % of $PdCl_2$ is used relative to the amount of compound (II).

Embodiment 24 provides for the process of any one of Embodiments 1-23, wherein about 10 mol % to about 200 mol % of the salt is used relative to the amount of compound (II).

Embodiment 25 provides for the process of any one of Embodiments 1-24, wherein about 95 mol % to about 105 mol % of the salt is used relative to the amount of compound (II).

Embodiment 26 provides for the process of any one of Embodiments 1-25, wherein about 100 mol % of the salt is used relative to the amount of compound (II).

Embodiment 27 provides for the process of any one of Embodiments 1-26, wherein the reacting of compound (II) in the presence of the catalyst and the organic solvent occurs at a temperature of about 60° C. to about 300° C.

Embodiment 28 provides for the process of any one of Embodiments 1-27, wherein the reacting of compound (II) in the presence of the catalyst and the organic solvent occurs at a temperature of about 155° C. to about 165° C.

Embodiment 29 provides for the process of any one of Embodiments 1-28, wherein the reacting of compound (II) in the presence of the catalyst and the organic solvent occurs at a temperature of about 160° C.

Embodiment 30 provides for the process of any one of Embodiments 1-29, wherein the reacting of compound (II) in the presence of the catalyst and the organic solvent occurs for about 15 minutes to about 36 hours.

Embodiment 31 provides for the process of any one of Embodiments 1-30, wherein the reacting of compound (II) in the presence of the catalyst and the organic solvent occurs for about 15 hours to about 17 hours.

Embodiment 32 provides for the process of any one of Embodiments 1-31, wherein the reacting of compound (II) in the presence of the catalyst and the organic solvent occurs for about 2 hours to about 4 hours.

Embodiment 33 provides a process of preparing olefins of the formula (III):

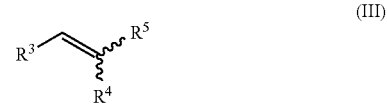

wherein:

$R^3$ is chosen from a substituted or unsubstituted $(C_1$-$C_{30})$ hydrocarbyl;

$R^4$ is chosen from a substituted or unsubstituted $(C_1$-$C_{20})$ hydrocarbyl;

$R^5$ is chosen from a substituted or unsubstituted $(C_1$-$C_{30})$ hydrocarbyl;

the process comprising:

reacting a compound of formula (IV)

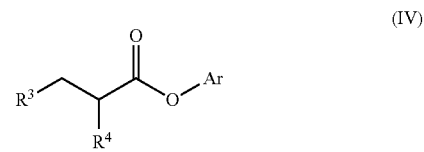

wherein Ar is chosen from

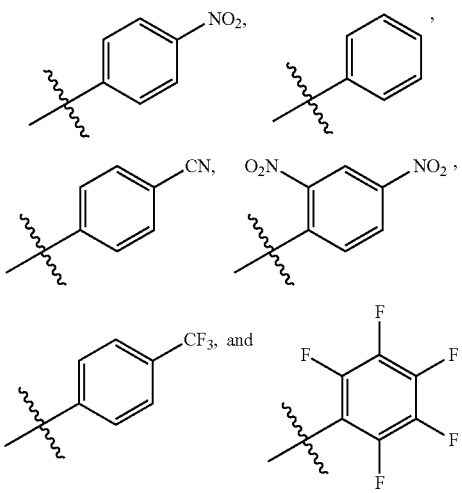

with a compound of formula (V)

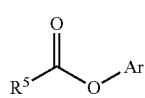

wherein Ar is chosen from

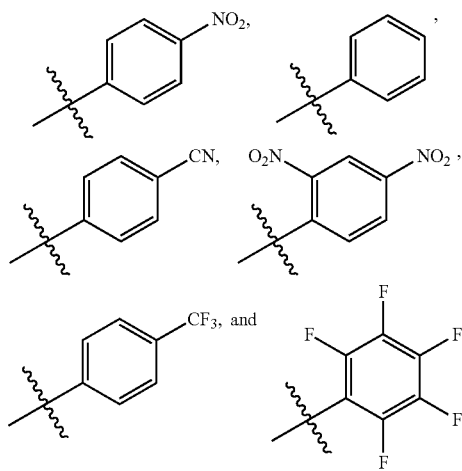

in the presence of a palladium-based catalyst, and an organic solvent.

Embodiment 34 provides for the process of Embodiment 33, wherein the preparation of the olefins of formula (III), as defined above, occurs in the absence of a phosphine ligand.

Embodiment 35 provides for the process of either one of Embodiments 33 or 34, wherein the palladium-based catalyst is formed in situ from a palladium(0) precursor.

Embodiment 36 provides for the process of any one of Embodiments 33-35, wherein the palladium-based catalyst is a palladium halide.

Embodiment 37 provides for the process for any one of Embodiments 33-36, wherein the palladium-based catalyst is $PdCl_2$ is chosen from $PdCl_2$, $Pd_2(dba)_3$. $PdI_2$, $PdBr_2$ and $(COD)PdCl_2$.

Embodiment 38 provides for the process of any one of Embodiments 33-37, wherein the reacting a compound of formula (IV) with a compound of formula (V) occurs in the presence of a salt.

Embodiment 39 provides for the process of any one of Embodiments 33-38, wherein the salt is an alkali metal halide, an alkaline-earth metal halide, and combinations thereof.

Embodiment 40 provides for the process of any one of Embodiments 33-39, wherein the salt is chosen from NaCl, NaBr, KCl, $CaCl_2$, LiCl, $MgCl_2$ and LiBr.

Embodiment 41 provides for the process of any one of Embodiments 33-40, wherein the salt is tetrabutylammonium bromide.

Embodiment 42 provides for the process of any one of Embodiments 33-41, wherein $R^3$ is chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$alkoxycarbonyl, and $(C_6-C_{27})$aryloxycarbonyl groups, each of which may be substituted by one or more groups chosen from Cl, F, Br, I, R', OR', SR', $NR'_2$, $SiR'_3$, COOR', (C=O)R', CN, and $CONR_2'$, wherein R' is chosen from H and $(C_1-C_{12})$alkyl.

Embodiment 43 provides for the process of any one of Embodiments 33-42, wherein $R^3$ is chosen from $(C_1-C_{20})$alkyl, $(C_3-C_5)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$alkoxycarbonyl, and $(C_6-C_{27})$aryloxycarbonyl groups.

Embodiment 44 provides for the process of any one of Embodiments 33-43, wherein $R^4$ is chosen from H, $(C_1-C_{20})$alkyl, and $(C_6-C_8)$aryl.

Embodiment 45 provides for the process of any one of Embodiments 33-44, wherein $R^4$ is chosen from H and phenyl.

Embodiment 46 provides for the process of any one of Embodiments 33-45, wherein $R^5$ is chosen from $(C_1-C_{20})$alkyl, $(C_3-C_5)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$alkoxycarbonyl, and $(C_6-C_{27})$aryloxycarbonyl groups, each of which may be substituted by one or more groups chosen from Cl, F, Br, I, R', OR', SR', $NR'_2$, $SiR'_3$, COOR', (C=O)R', CN, and $CONR_2'$, wherein R' is chosen from H and $(C_1-C_{12})$alkyl.

Embodiment 47 provides for the process of any one of Embodiments 33-46, wherein $R^5$ is chosen from $(C_6-C_{10})$aryl, $(C_7-C_{27})$arylalkyl, $(C_7-C_{27})$alkenylaryl groups.

Embodiment 48 provides for the process of any one of Embodiments 33-47, wherein $R^5$ is chosen from

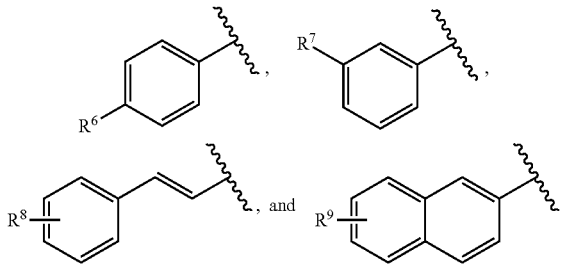

wherein:

$R^6$, $R^7$, $R^8$, and $R^9$ are each independently chosen from H, Cl, Br, F, $NO_2$, OH, OR', and a $(C_1-C_5)$alkyl, wherein $R^1$ is a $(C_1-C_5)$alkyl.

Embodiment 49 provides for the process of any one of Embodiments 33-48, wherein the organic solvent is chosen from 1,3-Dimethyl-3,4,5,6-tetrahydro-2(1H)-pyrimidinone, N,N-dimethylformamide and N,N-dimethylacetamide.

Embodiment 50 provides for the process of any one of Embodiments 33-49, wherein the olefin of formula (III) is cis with respect to groups $R^3$ and $R^5$.

Embodiment 51 provides for the process of any one of Embodiments 33-50, wherein the olefin of formula (III) is trans with respect to groups $R^3$ and $R^5$.

Embodiment 52 provides for the process of any one of Embodiments 33-51, wherein the olefin of formula (III) is a mixture of cis and trans isomers with respect to groups $R^3$ and $R^5$.

Embodiment 53 provides for the process of any one of Embodiments 33-52, wherein the mixture comprises about 75% to about 100% cis isomers with respect to groups $R^3$ and $R^5$.

Embodiment 54 provides for the process of any one of Embodiments 33-53, wherein the mixture comprises about 95% to about 100% cis isomers with respect to groups $R^3$ and $R^5$.

Embodiment 55 provides for the process of any one of Embodiments 33-54, wherein the mixture comprises about 75% to about 100% trans isomers with respect to groups $R^3$ and $R^5$.

Embodiment 56 provides for the process of any one of Embodiments 33-55, wherein the mixture comprises about 95% to about 100% trans isomers with respect to groups $R^3$ and $R^5$.

Embodiment 57 provides for the process of any one of Embodiments 33-56, wherein about 0.001 mol % to about 20 mol % of the catalyst is used relative to the amount of compound (IV).

Embodiment 58 provides for the process of any one of Embodiments 33-57, wherein about 5 mol % to about 10 mol % of $PdCl_2$ is used relative to the amount of compound (IV).

Embodiment 59 provides for the process of any one of Embodiments 33-58, wherein about 10 mol % to about 200 mol % of the salt is used relative to the amount of compound (IV).

Embodiment 60 provides for the process of any one of Embodiments 33-59, wherein about 95 mol % to about 105 mol % of the salt is used relative to the amount of compound (IV).

Embodiment 61 provides for the process of any one of Embodiments 33-60, wherein about 100 mol % of the salt is used relative to the amount of compound (IV).

Embodiment 62 provides for the process of any one of Embodiments 33-61, wherein the reacting of compound (IV) with compound (V) in the presence of the catalyst and the organic solvent occurs at a temperature of about 60° C. to about 300° C.

Embodiment 63 provides for the process of any one of Embodiments 33-62, wherein the reacting of compound (IV) with compound (V) in the presence of catalyst and the organic solvent occurs at a temperature of about 155° C. to about 165° C.

Embodiment 64 provides for the process of any one of Embodiments 33-63, wherein the reacting of compound (IV) with compound (V) in the presence of the catalyst and the organic solvent occurs at a temperature of about 160° C.

Embodiment 65 provides for the process of any one of Embodiments 33-64, wherein the reacting of compound (IV) with compound (V) in the presence of the catalyst and the organic solvent occurs for about 1 hour to about 36 hours.

Embodiment 66 provides for the process of any one of Embodiments 33-65, wherein the reacting of compound (IV) with compound (V) in the presence of the catalyst and the organic solvent occurs for about 15 hours to about 17 hours.

Embodiment 67 provides for the process of any one of Embodiments 33-66, wherein the reacting of compound (IV) with compound (V) in the presence of the catalyst and the organic solvent occurs for about 2 hours to about 4 hours.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A process of preparing an olefin of formula (I):

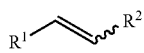 (I)

wherein:
R$^1$ is chosen from a substituted or unsubstituted (C$_1$-C$_{30}$) hydrocarbyl;
R$^2$ is chosen from a substituted or unsubstituted (C$_1$-C$_{20}$) hydrocarbyl;
the process comprising:
reacting a compound of formula (II)

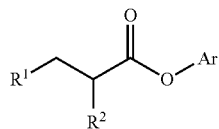 (II)

wherein Ar is chosen from

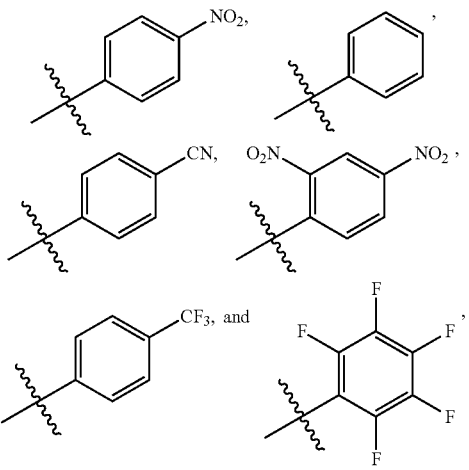

in the presence of a palladium-based catalyst and an organic solvent, to provide the compound of the formula (I).

2. The process of claim 1, wherein the reacting of the compound of the formula (II) is also conducted in the presence of one or more ligands, wherein the preparation of the olefin of the formula (I) in the presence of the one or more ligands has a selectivity to α-olefins of at least about 60%.

3. The process of claim 2, wherein the one or more ligands comprise one or more of: one or more phenylphosphine-based ligands or one or more heterocyclic carbene ligands.

4. The process of claim 1, wherein the reacting of the compound of the formula (II) further occurs in the presence a salt.

5. The process of claim 4, wherein the salt is chosen from an alkali metal halide, an alkaline-earth metal halide, tetrabutylammonium bromide, or combinations thereof.

6. The process of claim 1, wherein R$^1$ is chosen from (C$_1$-C$_{20}$)alkyl, (C$_3$-C$_8$)cycloalkyl, (C$_2$-C$_{12}$)alkenyl, (C$_2$-C$_{20}$)alkynyl, (C$_6$-C$_{10}$)aryl, (C$_7$-C$_{27}$)alkylaryl, (C$_7$-C$_{27}$)alkylaryl, (C$_2$-C$_{20}$)alkylcarbonyloxy, (C$_6$-C$_{27}$)arylcarbonyloxy, (C$_2$-C$_{20}$)alkoxycarbonyl, or (C$_6$-C$_{27}$)aryloxycarbonyl groups.

7. The process of claim 6, wherein one or more of the (C$_1$-C$_{20}$)alkyl, the (C$_3$-C$_8$)cycloalkyl, the (C$_2$-C$_{12}$)alkenyl, the (C$_2$-C$_{20}$)alkynyl, the (C$_6$-C$_{10}$)aryl, the (C$_7$-C$_{27}$)arylalkyl, the (C$_7$-C$_{27}$)alkylaryl, the (C$_2$-C$_{20}$)alkylcarbonyloxy, the (C$_6$-C$_{27}$)arylcarbonyloxy, the (C$_2$-C$_{20}$)alkoxycarbonyl, or the (C$_6$-C$_{27}$)aryloxycarbonyl groups of R$^1$ are substituted by one or more groups chosen from Cl, F, Br, I, R', OR', SR', NR'$_2$, SiR'$_3$, COOR', (C=O)R', CN, or CONR$_2$', wherein R' is chosen from H or a (C$_1$-C$_{12}$)alkyl.

8. The process of claim 1, wherein in R$^2$ is chosen from H, a (C$_1$-C$_{20}$)alkyl, a (C$_6$-C$_8$)aryl, or a phenyl group.

9. The process of claim 1, wherein the preparation of the olefin of the formula (I) occurs in the absence of a phosphine ligand.

10. A process of preparing an olefin of formula (III):

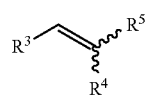 (III)

wherein:
R$^3$ is chosen from a substituted or unsubstituted (C$_1$-C$_{30}$)hydrocarbyl;
R$^4$ is chosen from a substituted or unsubstituted (C$_1$-C$_{20}$)hydrocarbyl;
R$^5$ is chosen from a substituted or unsubstituted (C$_1$-C$_{30}$)hydrocarbyl;
the process comprising:
reacting a compound of formula (IV)

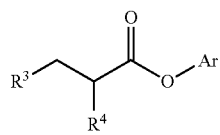 (IV)

wherein Ar is chosen from

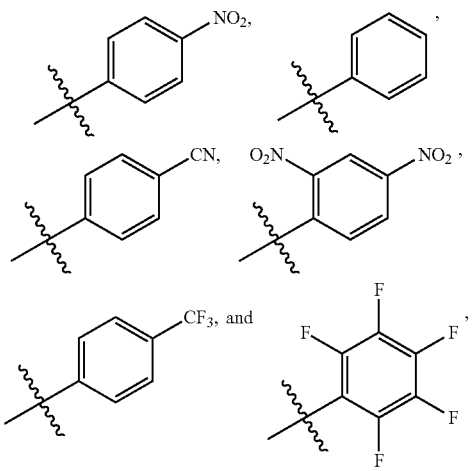

with a compound of formula (V)

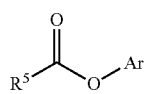
(V)

wherein Ar is chosen from

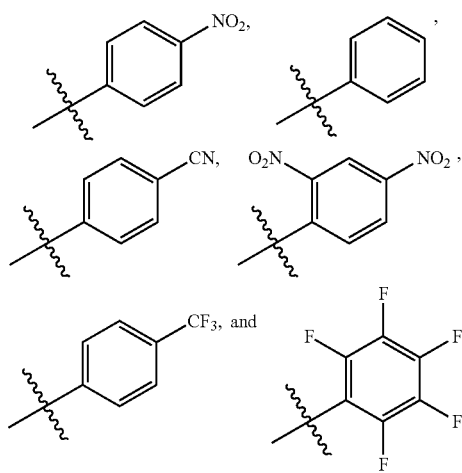

in the presence of a palladium-based catalyst, and an organic solvent.

11. The process of claim 10, wherein the reacting of the compound of the formula (IV) with the compound of the formula (V) is also conducted in the presence of one or more ligands.

12. The process of claim 11, wherein the one or more ligands comprise one or more of: one or more phenylphosphine-based ligands or one or more heterocyclic carbene ligands.

13. The process of claim 10, wherein the reacting of the compound of the formula (IV) with the compound of formula (V) occurs in the presence of a salt.

14. The process of claim 13, wherein the salt comprises at least one of: an alkali metal halide, an alkaline-earth metal halide, tetrabutylammonium bromide or combinations thereof.

15. The process of claim 10, wherein $R^3$ is chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_2-C_{20})$alkylcarbonyloxy, $(C_6-C_{27})$arylcarbonyloxy, $(C_2-C_{20})$alkoxylcarbonyl, and $(C_6-C_{27})$aryloxycarbonyl groups.

16. The process of claim 15, wherein one or more of the $(C_1-C_{20})$alkyl, the $(C_3-C_8)$cycloalkyl, the $(C_2-C_{12})$alkenyl, the $(C_2-C_{20})$alkynyl, the $(C_6-C_{10})$aryl, the $(C_7-C_{27})$arylalkyl, the $(C_7-C_{27})$alkylaryl, the $(C_2-C_{20})$alkylcarbonyloxy, the $(C_6-C_{27})$arylcarbonyloxy, the $(C_2-C_{20})$alkoxycarbonyl, or the $(C_6-C_{27})$aryloxycarbonyl groups of $R^3$ are substituted by one or more groups chosen from Cl, F, Br, I, R', OR', SR', NR'$_2$, SiR'$_3$, COOR', (C=O)R', CN, and CONR$_2$', wherein R' is chosen from H and $(C_1-C_{12})$alkyl.

17. The process of claim 10, wherein $R^4$ is chosen from H, a $(C_1-C_{20})$alkyl, a $(C_6-C_8)$aryl, or a phenyl group.

18. The process of claim 10, wherein $R^5$ is chosen from $(C_1-C_{20})$alkyl, $(C_3-C_8)$cycloalkyl, $(C_2-C_{12})$alkenyl, $(C_2-C_{20})$alkynyl, $(C_6-C_{10})$aryl, $(C_7-C_{27})$arylalkyl, $(C_7-C_{27})$alkylaryl, $(C_7-C_{27})$alkenylaryl, $(C_2-C_{20})$alkylcarbonyloxy, $(C_6-C_{27})$arylcarbonyloxy, $(C_2-C_{20})$alkoxycarbonyl, and $(C_6-C_{27})$aryloxycarbonyl groups.

19. The process of claim 18, wherein one or more of the $(C_1-C_{20})$alkyl, the $(C_3-C_8)$cycloalkyl, the $(C_2-C_{12})$alkenyl, the $(C_2-C_{20})$alkynyl, the $(C_6-C_{10})$aryl, the $(C_7-C_{27})$arylalkyl, the $(C_7-C_{27})$alkylaryl, the $(C_7-C_{27})$alkenylaryl, the $(C_2-C_{20})$alkylcarbonyloxy, the $(C_6-C_{27})$arylcarbonyloxy, the $(C_2-C_{20})$alkoxycarbonyl, or the $(C_6-C_{27})$aryloxycarbonyl groups of $R^5$ are substituted by one or more groups chosen from Cl, F, Br, I, R', OR', SR', NR'$_2$, SiR'$_3$, COOR', (C=O)R', CN, and CONR$_2$', wherein R' is chosen from H and a $(C_1-C_{12})$alkyl group.

20. The process of claim 10, wherein $R^5$ is chosen from

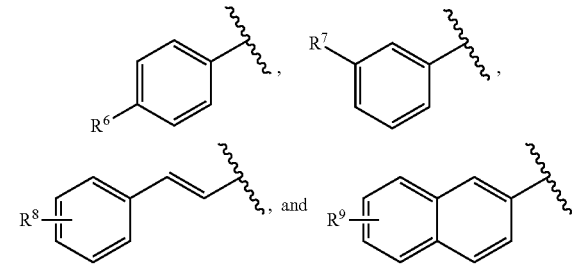

wherein $R^6$, $R^7$, $R^8$, and $R^9$ are each independently chosen from H, Cl, Br, F, NO$_2$, OH, OR' and a $(C_1-C_5)$alkyl, and wherein R' is a $(C_1-C_5)$alkyl group.

21. The process of claim 10, wherein the preparation of the olefin of the formula (III) occurs in the absence of a phosphine ligand.

* * * * *

UNITED STATES PATENT AND TRADEMARK OFFICE
CERTIFICATE OF CORRECTION

PATENT NO. : 9,718,763 B2
APPLICATION NO. : 14/990308
DATED : August 1, 2017
INVENTOR(S) : Tolman et al.

It is certified that error appears in the above-identified patent and that said Letters Patent is hereby corrected as shown below:

In the Specification

In Column 1, Line 42, after "document.", insert --¶The patent or application file contains at least one drawing executed in color. Copies of this patent or patent application publication with color drawing(s) will be provided by the Office upon request and payment of the necessary fee.--

In Column 3, Line 2, delete "groups:" and insert --groups;-- therefor

In Column 3, Line 4, delete "groups." and insert --groups,-- therefor

In Column 3, Line 22, delete ""olefin."" and insert --"olefin,"-- therefor

In Column 3, Line 31, delete "-C(CH$_3$)-CH(CH$_3$)," and insert -- -C(CH$_3$)=CH(CH$_3$),-- therefor In Column 4, Line 22, after "heptalenyl", insert --,--

In Column 4, Line 23, after "naphthacenyl", insert --,--

In Column 5, Line 45, delete ""halogen."" and insert --"halogen,"-- therefor

In Column 5, Line 54, after "1,2-dichloroethyl", insert --,--

In Column 6, Line 65, after "(COD)PdCl$_2$", insert --.--

In Column 7, Line 10-11, delete "(C$_2$-C$_{20}$) alkoxycarbonyl," and insert --(C$_2$-C$_{20}$)alkoxycarbonyl,-- therefor In Column 7, Line 20, delete "(C$_2$-C$_{20}$) alkoxycarbonyl," and insert --(C$_2$-C$_{20}$)alkoxycarbonyl,-- therefor Signed and Sealed this
Twenty-first Day of April, 2020

Andrei Iancu
*Director of the United States Patent and Trademark Office*

CERTIFICATE OF CORRECTION (continued)
U.S. Pat. No. 9,718,763 B2

In Column 7, Line 22, delete "embodiments." and insert --embodiments,-- therefor In Column 7, Line 25, after "embodiments", insert --,--

In Column 7, Line 28-29, delete ""DMPU"and" 1,3-Dimethyl-3,4,5,6-tetrahydro-2(1H)-pyrimidinone,"" and insert --"DMPU" and "1,3-Dimethyl-3,4,5,6-tetrahydro-2(1H)-pyrimidinone,"-- therefor In Column 10, Line 22, delete "($C_2$-$C_{20}$) alkoxycarbonyl," and insert --($C_2$-$C_{20}$)alkoxycarbonyl,-- therefor In Column 10, Line 30, delete "($C_2$-$C_{20}$) alkoxycarbonyl," and insert --($C_2$-$C_{20}$)alkoxycarbonyl,-- therefor In Column 10, Line 36, delete "($C_2$-$C_{20}$) alkoxycarbonyl," and insert --($C_2$-$C_{20}$)alkoxycarbonyl,-- therefor In Column 10, Line 39, delete "$R^1$" and insert --R'-- therefor In Column 10, Line 42, delete "embodiments." and insert --embodiments,-- therefor In Column 10, Line 45-46, delete "($C_2$-$C_{20}$) alkoxycarbonyl," and insert --($C_2$-$C_{20}$)alkoxycarbonyl,-- therefor In Column 11, Line 10, delete "1,3-Dimethyl-3,4,5,6-tetrahydro-2(1H)-pyrimidinone." and insert --1,3-Dimethyl-3,4,5,6-tetrahydro-2(1H)-pyrimidinone,-- therefor In Column 12, Line 65, delete "a" and insert --α-- therefor In Column 12, Line 66, delete "carbon)." and insert --carbon),-- therefor In Column 13, Line 14, delete "catalyst." and insert --catalyst,-- therefor In Column 13, Line 51, delete "($PH_3$)." and insert --($PH_3$),-- therefor In Column 15, Line 2, delete "ligands." and insert --ligands,-- therefor In Column 15, Line 51, delete "vs," and insert --vs.-- therefor In Column 15, Line 62, delete "5 mol %)." and insert --5 mol %),-- therefor In Column 16, Line 5, after "funnel", insert --,--

In Column 19, Line 53, delete "1-octane." and insert --1-octene.-- therefor

In Column 22, Line 36, delete "$PdCl_2$." and insert --$PdCl_2$,-- therefor

CERTIFICATE OF CORRECTION (continued)
U.S. Pat. No. 9,718,763 B2

In Column 22, Line 56-57, delete "$(C_2$-$C_{20})$ alkoxycarbonyl," and insert --$(C_2$-$C_{20})$alkoxycarbonyl,-- therefor In Column 22, Line 66-67, delete "$(C_2$-$C_{20})$ alkoxycarbonyl," and insert --$(C_2$-$C_{20})$alkoxycarbonyl,-- therefor In Column 25, Line 65-66, delete "$(C_2$-$C_{20})$ alkoxycarbonyl," and insert --$(C_2$-$C_{20})$alkoxycarbonyl,-- therefor In Column 26, Line 6, delete "$(C_3$-$C_5)$cycloalkyl," and insert --$(C_3$-$C_8)$cycloalkyl,-- therefor In Column 26, Line 8-9, delete "$(C_2$-$C_{20})$ alkoxycarbonyl," and insert --$(C_2$-$C_{20})$alkoxycarbonyl,-- therefor In Column 26, Line 19, delete "$(C_3$-$C_5)$cycloalkyl," and insert --$(C_3$-$C_8)$cycloalkyl,-- therefor In Column 26, Line 21-22, delete "$(C_2$-$C_{20})$ alkoxycarbonyl," and insert --$(C_2$-$C_{20})$alkoxycarbonyl,-- therefor In Column 26, Line 49, delete "$R^1$" and insert --R'-- therefor In Column 28, Line 23, delete ""second."" and insert --"second,"-- therefor In the Claims In Column 29, Line 61, in Claim 4, before "a salt.", insert --of--

In Column 29, Line 67, in Claim 6, delete "$(C_7$-$C_{27})$alkylaryl," and insert --$(C_7$-$C_{27})$arylalkyl,-- therefor In Column 30, Line 13, in Claim 8, after "wherein", delete "in"

In Column 32, Line 2, in Claim 15, delete "$(C_2$-$C_{20})$alkoxylcarbonyl," and insert --$(C_2$-$C_{20})$alkoxycarbonyl,-- therefor